United States Patent
Vasudevan et al.

(10) Patent No.: US 6,759,546 B1
(45) Date of Patent: Jul. 6, 2004

(54) 3,5-DI-ISO-PROPYL-HEPTATRIENOIC ACID DERIVATIVES HAVING SERUM GLUCOSE REDUCING ACTIVITY

(75) Inventors: Jayasree Vasudevan, Anaheim, CA (US); Richard L. Beard, Newport Beach, CA (US); Haiqing Yuan, Irvine, CA (US); Roshantha A. Chandratratna, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/357,911

(22) Filed: Feb. 4, 2003

(51) Int. Cl.⁷ .............................................. C07C 69/76
(52) U.S. Cl. ......................................... 560/55; 514/532
(58) Field of Search ............................. 560/55; 514/532

(56) References Cited

U.S. PATENT DOCUMENTS

| | | |
|---|---|---|
| 5,455,265 A | 10/1995 | Chandraratna |
| 5,721,103 A | 2/1998 | Boehm et al. |
| 5,801,253 A | 9/1998 | Klaus et al. |
| 6,114,533 A | 9/2000 | Vuligonda et al. |
| 6,326,397 B1 | 12/2001 | Bollag et al. |

FOREIGN PATENT DOCUMENTS

| | | |
|---|---|---|
| WO | WO-93-11755 | 6/1993 |
| WO | WO-97-12853 | 4/1997 |
| WO | WO-01-19770 | 3/2001 |

OTHER PUBLICATIONS

Mangelsdorf et al. The Retinoid Receptors In: THe Retinoids pp.: 319–349 (1994).
Dawson et al. Chemistry and Biology of Synthetic Retinoids pp.: 324–356 (1990).
Mukherjee et al. Nature vol. 386 pp.: 407–410 (1997).
Heyman et al. Cell vol. 68 pp.: 397–406 (1992).
Allegretto et al. Journal of Biological Chemistry vol. 268 pp.: 26625–26633 (1993).
Cheng et al. Biochemical Pharmacology vol. 22 pp.: 3099–3108 (1973).
Feigner et al. Focus vol. 11 pp.: 21–24 (1989).
Synthesis pp.: 47–55 (1995).

*Primary Examiner*—Paul J. Killos
(74) *Attorney, Agent, or Firm*—Gabor L. Szekeres; Robert J. Baran; Martin A. Voet

(57) ABSTRACT

Compounds of the formula

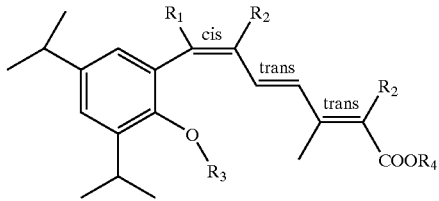

where the variables have the meaning defined in the specification are capable of reducing serum glucose levels in diabetic mammals without the undesirable side effect of reducing serum thyroxine levels.

17 Claims, No Drawings

3,5-DI-ISO-PROPYL-HEPTATRIENOIC ACID DERIVATIVES HAVING SERUM GLUCOSE REDUCING ACTIVITY

BACKGROUND OF THE INVENTION

FIELD OF INVENTION

The present invention relates to compounds that have the property of reducing serum glucose and serum triglyceride levels in diabetic mammals without the undesirable property of reducing serum thyroxine levels. More particularly, the present invention relates to 3,5-di-iso-propyl-heptatrienoic acid derivatives having the above-noted biological property.

Compounds that have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXR_\beta$ and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property.

For a general overview of the retinoid receptors see Mangelsdorf et al. (1994) The Retinoid Receptors In: The Retinoids, edited by Sporn et al. p 319–349. Raven Press, Ltd., New York. For another general overview see Dawson and William H. Okamura, Chemistry and Biology of Synthetic Retinoids, published by CRC Press Inc., 1990, pages 324–356. The following further patents are of interest as background to the present invention: U.S. Pat. Nos. 5,721, 103; 5,801,253; 6,326,397; PCT Publications WO 97/12853 and WO 01/19770.

Relatively recently it has become known that certain retinoid compounds are capable of reducing serum glucose levels in diabetic mammals. Mukheijee, R.; Davies, P. J.; Crombie, D. L. Bishoff, E. D.; Cesario, R. M.; Jow Hamann, L. G.; Boehm, M. F.; Mondon, C. E.; Nadzan, A. M.; Paterniti, J. R. Jr.; Heyman, R. A. Sensitization of Diabetic and Obese Mice to Insulin by Retinoid X Receptor Agonists. Nature 1997, 386 (6623), 407–410. The compound (2E, 4E, 1'S, 2'S)-3-methyl-5-[2'-methyl-2'-(5, 5,8,8-tetramethyl-5,6, 7,8-tetrahydro-naphthalen-2-yl)-cyclopropyl]-penta-2,4-dienoic acid, described in U.S. Pat. No. 6,114,533 has this property. A disadvantage of the prior art retinoid compounds that reduce serum glucose levels is that their administration usually also results in the pharmacologically undesirable reduction of seruim thyroxine levels and in a transient increase in serum triglyceride levels. The present invention is directed to novel compounds that do not have these undesirable side effects.

SUMMARY OF THE INVENTION

The present invention relates to compounds of Formula 1

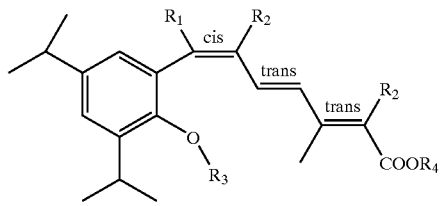

Formula 1 where $R_1$ is alkyl of 1 to 3 carbons;
$R_2$ is independently H or F;
$R_3$ is propyl or iso-propyl, and
$R_4$ is is H, alkyl of 1 to 6 carbons, $CH_2OR_5$ or $CH_2OCOR_5$ where $R_5$ is alkyl of 1 to 3 carbons, or a pharmaceutically acceptable salt of said compound.

The present invention also relates to pharmaceutical compositions incorporating the compounds of Formula 1 and to methods of treatment of diabetic mammals with pharmaceutical compositions containing one or more compounds of Formula 1 to reduce serum glucose levels in said mammals. The present invention also relates to the methods of using the compounds of the invention to treat diseases and conditions that are responsive to treatment by retinoids.

DETAILED DESCRIPTION OF THE INVENTION

GENERAL EMBODIMENTS AND SYNTHETIC METHODOLOGY

Definitions

The term alkyl refers to and covers any and all groups which are known as normal alkyl and branched-chain alkyl.

A pharmaceutically acceptable salt may be prepared for any compound in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

The compounds of the present invention include olephinic double bonds about which trans and cis (E and Z) stereoisomerism can exist. The compounds of the present invention have the specific orientations of substituents relative to the double bonds as is indicated in the name of the respective compound, and/or by specific showing in the structural formula of the orientation of the substituents relative to the respective double bonds.

Some of the compounds of the present invention may contain one or more chiral centers and therefore may exist in enantiomeric and diastereomeric forms. The scope of the present invention is intended to cover the trans and cis (E and Z) isomers as specifically shown and/or named, as well as pure enantiomers (optical isomers), diastereomers, mixtures of diastereomers and racemic mixtures of enantiomers.

Reaction Scheme 1 discloses a presently preferred synthetic route to compounds of the invention. Although this synthetic route is general, the cis and/or trans isomerism of the compounds of the invention is indicated properly in the formulas.

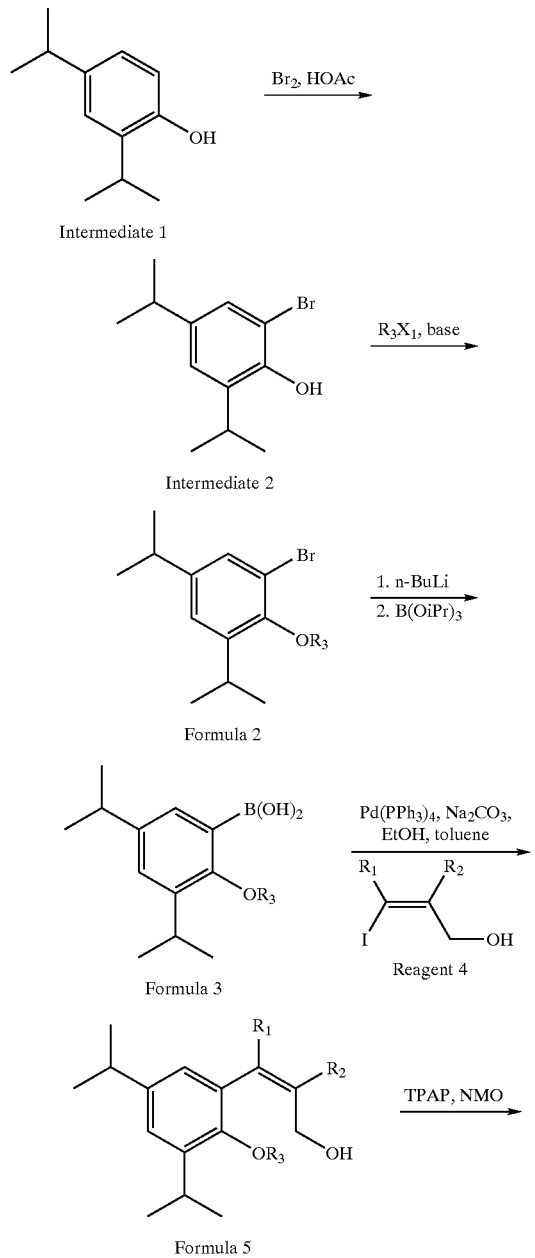

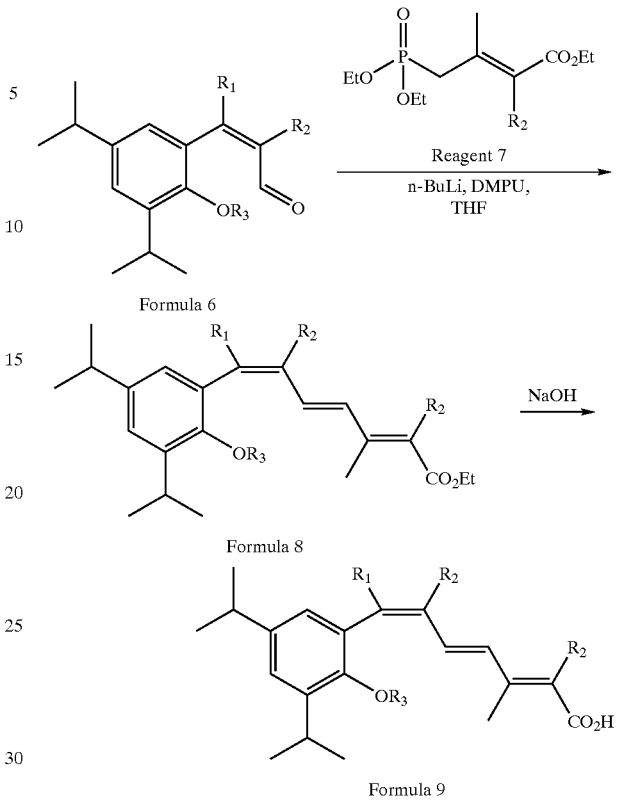

Referring now to Reaction Scheme 1, the starting material is 2,4-diisopropyl-phenol (Intermediate 1 that can be obtained from 3,5-diisopropylsalicylic acid, as is shown in Reaction Scheme 3 below) is brominated in acetic acid as a solvent to yield 2-bromo4,6-diisopropyl-phenol (Intermediate 2).

Bromo-4,6-diisopropyl-phenol is then reacted with a reagent of the formula $R_3X_1$ in the presence of base, to give 1-bromo-3,5-diisopropyl-2-alkyloxy-benzene (Formula 2). The variable $R_3$ is defined as in connection with Formula 1 and $X_1$ is a leaving group. In the synthesis of the presently preferred compounds of the invention $R_3X_1$ is propyl iodide. The compound of Formula 2 is then reacted with tri-isopropylborate in the presence of strong base, such as butyl lithium, at cold temperature to provide 2-alkoxy-3,5-diisopropyl-phenylboronic acid (Formula 3). The boronic acid derivative (Formula 3) is reacted with a 3-iodo-pent-en-1-ol derivative (Reagent 4) in the presence tetrakis (triphenylphosphine)palladium (0) catalyst and base (such as sodium carbonate) to provide a 3-(3,5-diisopropyl-2-alkoxy-phenyl)-pent-2-en-1-ol derivative (Formula 5). The variables $R_1$ and $R_2$ of Reagent 4 are defined as in connection with Formula 1. 3-Iodo-pent-2-en-1-ol (available from *Synthesis*, 1995, 47–55.) serves as an example and is utilized in the synthesis of a preferred compound of the invention. Other reagents within the scope of the formula of Reagent 4 are either available commercially, or from the chemical literature, or can be synthesized by one of ordinary skill in the art by apparent modifications of known literature procedures.

The 3-(3,5-diisopropyl-2-alkoxy-phenyl)-pent-2-en-1-ol derivative (Formula 5) is subjected to oxidation with N-methylmorpholine-N-oxide (NMO) in the presence of catalytic amounts of tetrapropylammonium peruthenate (TPAP) to give a 3-(3,5-diisopropyl-2-alkoxy-phenyl)-pent-2-enal derivative (Formula 6). The aldehyde of Formula 6 is subjected to a Horner Emmons reaction with Reagent 7 where the variable $R_2$ is defined as in connection with Formula 1. The Horner Emmons reaction per se is well known in the art, and is conducted in an aprotic solvent, such as heptane or tetrahydrofuran (THF) or mixtures of aprotic solvents, in the presence of strong base, such an n-butyl lithium or lithium diisopropylamide (LDA). 4-diethoxy-phosphoryl)-3-methyl-but-2-enoic acid ethyl ester ($R_2$=H, available from JOC, 1974, 39, 821) and the corresponding 2-fluoro derivative serve as examples for Reagent 7. The product of the Horner Emmons reaction is a 7-(3,5-diisopropyl-2-alkoxy-phenyl)-3-methyl-nona-2,4,6-trienoic acid ethyl ester derivative of Formula 8 which is a compound of the invention, within the scope of Formula 1. Saponification of the ester compound of Formula 8 provides the free acid compounds of the invention (or pharmaceutically acceptable salts thereof) as shown by Formula 9.

SPECIFIC EMBODIMENTS OF THE COMPOUNDS OF THE INVENTION

Referring now to Formula 1, in the presently preferred compounds of the invention the $R_1$ group is methyl or ethyl, $R_2$ is H and $R_3$ is propyl. $R_4$ is preferably hydrogen, or alkyl of 1 to 3 carbons, or a pharmaceutically acceptable salt of the carboxylic acid compound.

The synthesis of the presently most preferred compounds of the invention is shown in Reaction Schemes 2 and 3 and a detailed description of the experimental procedures for synthesizing these most preferred exemplary compounds is also provided below. Reaction Scheme 2 follows the general synthetic route of Reaction Scheme 1 whereas Reaction Scheme 3 discloses a synthetic route which is presently preferred for the synthesis of Compound 16.

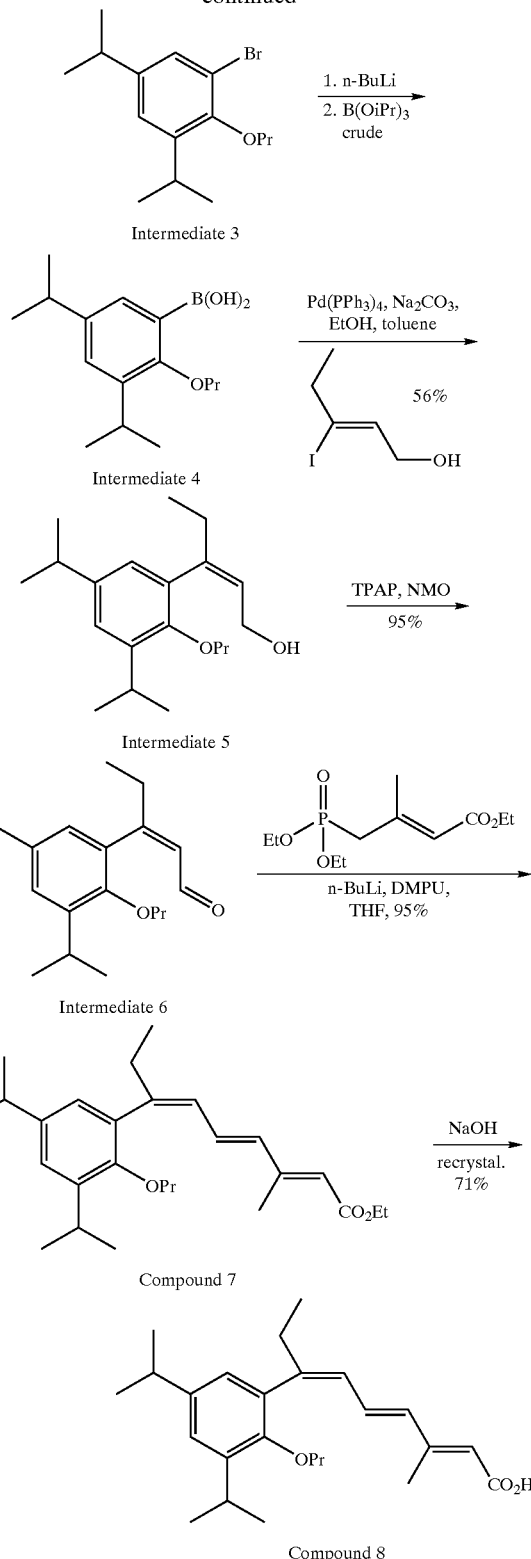

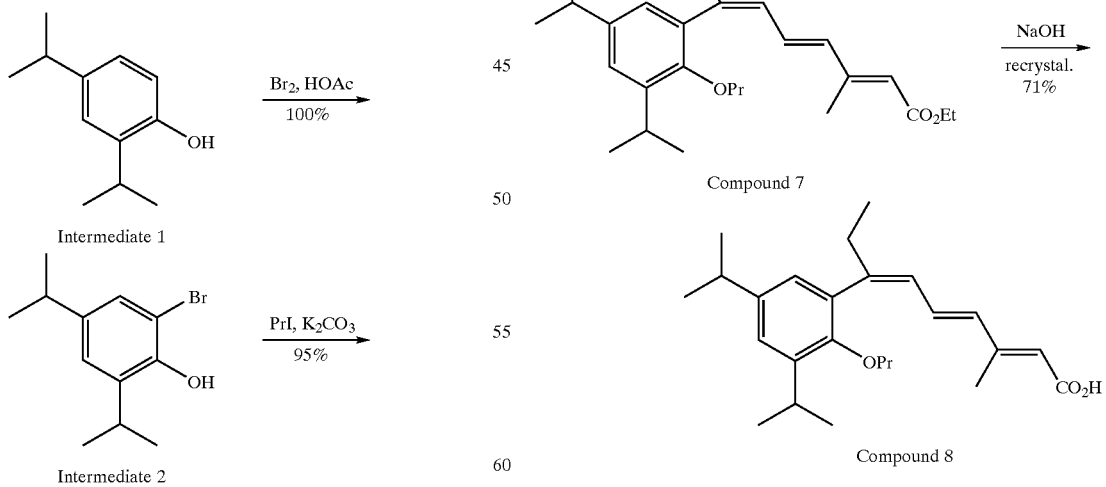

Reaction Scheme 3

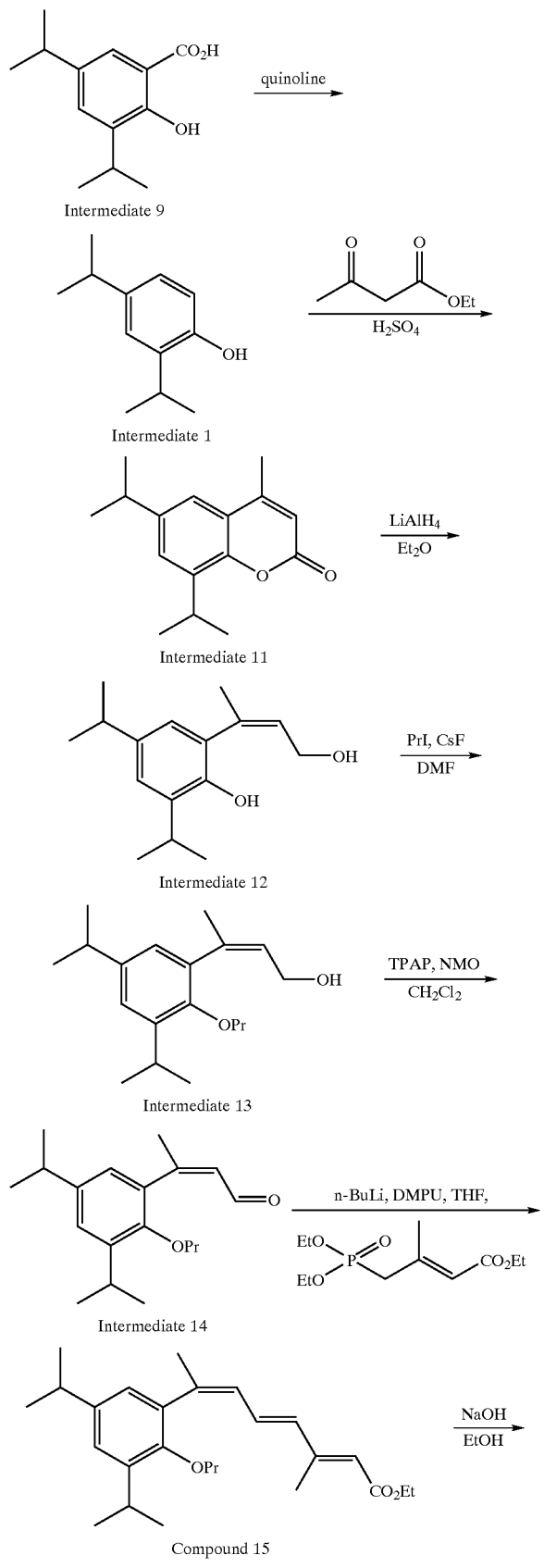

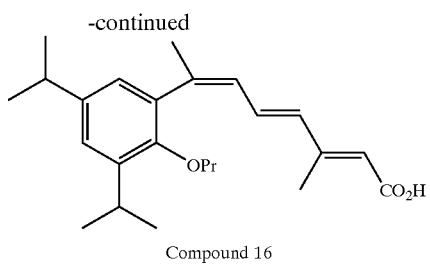

Compound 16

Experimental Procedures For Synthesizing the Exemplary Compounds of the Invention 2-Bromo-4,6-diisopropyl-phenol (Intermediate 2)

To a solution of 2,4-diisopropyl-phenol (Intermediate 1, 10.0 g, 56 mmol) in acetic acid (20 mL) was added bromine (3.5 mL, 67 mmol) at 0° C. The mixture was stirred at 0° C. for 15 min, quenched with water and extracted with EtOAc. The organic layer was washed successively with NaOH (4M, 85 mL), NaHSO$_3$, and brine, dried over Na$_2$SO$_4$, and concentrated in vacuo. The residue was purified by flash column chromatography on silica gel (hexanes) to yield the title compound as a light yellow oil (14.5 g, 100%).

$^1$H NMR (300 MHz, CDCl$_3$): δ 1.21 (d, J=7.0 Hz, 6H), 1.24 (d, J=7.0 Hz, 6H), 2.81 (hept, J=7.0 Hz, 1H), 3.29 (hept, J=7.0 Hz, M1), 5.41 (s, 1H), 6.98 (d, J=2.1 Hz, 1H), 7.15 (d, J=2.1 Hz, 1H).

1-Bromo-3,5-diisopropyl-2-propoxy-benzene (Intermediate 3)

A mixture of 2-bromo-4,6-diisopropyl-phenol (Intermediate 2, 14.5 g, 56 mmol), 1-iodopropane (16.5 mL, 169 mmol), and K$_2$CO$_3$ (38.6 g, 280 mmol) in acetone (100 mL) was stirred at room temperature for 64 h. The solvent was removed in vacuo, and the residue was taken up in CHCl$_3$ and filtered. The filtrate was concentrated in vacuo and the crude product was purified by flash column chromatography on silica gel (hexanes) to yield the title compound as a colorless oil (16.0 g, 95%).

$^1$H NMR (300 MHz, CDCl$_3$): δ 1.08 (t, J=7.5 Hz, 3H), 1.22 (2d, J=7.0 Hz, 12H), 1.86 (m, 2H), 2.83 (hept, J=7.0 Hz, 1H), 3.32 (hept, J=7.0 Hz, 1H), 3.83 (t, J=6.6 Hz, 2H), 7.02 (d, J=2.1 Hz, 1H), 7.22 (d, J=2.3 Hz, 1H).

2-Propoxy-3,5-diisopropyl-phenylboronic acid (Intermediate 4)

To a solution of n-BuLi (1.6 M in hexane, 40 mL, 64.2 mmol) in THF (150 mL) at −78° C. was added 1-bromo-3,5-diisopropyl-2-propoxy-benzene (Intermediate 3,16.0 g, 53.5 mmol) in THF (50 mL and 10 mL rinse) slowly. Thereafter 0.5 h triisopropyl borate (24.7 mL, 107 mmol) in THF (40 mL) was added slowly and the reaction was stirred at −78° C. for 1 h and at room temperature for 2 h. The reaction was then treated with 3M HCl (200 mL) at room temperature for 1.5 h, and extracted with EtOAc (×2). The organic layer was washed with brine, dried over Na$_2$SO$_4$, and concentrated in vacuo. The crude product was washed with hexane to give 3.28 g of the title compound as a white solid. The hexane solution was filtered through a pad of SiO$_2$ to give additional 11.0 g of the title compound as a yellow slurry containing minor impurities. This crude material was used in the next step without flirter purification.

$^1$H NMR (300 MHz, CDCl$_3$): δ 1.07 (t, J=7.5 Hz, 3H), 1.24 (d, J=6.7 Hz, 6H), 1.25 (d, J=6.7 Hz, 6H), 1.86 (m, 2), 2.89 (hept, J=7.0 Hz, 1H), 3.26 (hept, J=7.0 Hz, 1H), 3.76 (t, J=6.7 Hz, 2H), 5.91 (br s, 2H), 7.24 (d, J=2.6 Hz, 1H), 7.50 (d, J=2.4 Hz, 1H).

3-(3,5-Diisopropyl-2-propoxy-phenyl)-pent-2-en-1-ol (Intermediate 5)

A mixture of 2-propoxy-3,5-diisopropyl-phenylboronic acid (Intermediate 4, 3.28 g, 12.4 mmol), 3-iodo-pent-2-en-1-ol (3.95 g, 18.6 mmol), Pd(PPh$_3$)$_4$ (720 mg, 0.62 mmol), and Na$_2$CO$_3$ (2M, 31 mL, 62 mmol) in toluene (40 mL) and EtOH (30 mL) was heated to 92° C. for overnight. The reaction was cooled to room temperature and extracted with EtOAc (×3). The organic layer was washed with brine, dried over Na$_2$SO$_4$, and concentrated in vacuo. The additional 1.10 g of Intermediate 4 as described above was subjected to the same reaction conditions to also give crude product. The combined crude products were purified by flash column chromatography on silica gel (10% EtOAc-hexanes) to yield the title compound as a light brown oil (9.2 g, 56% over 2 steps).

$^1$H NMR(300MHz, CDCl$_3$): δ 0.99 (t, J=7.3 Hz, 3H), 1.11 (t, J=7.5 Hz, 3H), 1.23 (2d, J=6.7 Hz, 12H), 1.73 (m, 2H), 2.43 (br q, J=7.3 Hz, 2H), 2.84 (hept, J=6.7 Hz, 1H), 3.31 (hept, J=7.0 Hz, 1H), 3.62 (br s, 1H), 5.79 (br t, J=7.5 Hz, 1H), 6.72 (d, J=2.4 Hz, 1H), 7.01 (d, J=2.4 Hz, 1H).

3-(3,5-Diisopropyl-2-propoxy-phenyl)-pent-2-enal (Intermediate 6)

To a solution of 3-(3,5-diisopropyl-2-propoxy-phenyl)-pent-2-en-1-ol (Intermediate 5, 9.2 g, 30.3 mmol) and NMO (10.6 g, 90.8 mmol) in CH$_2$Cl$_2$ (50 mL) at 0° C. was added catalytic amount of TPAP. The reaction was stirred at room temperature for 1.5 h, and then loaded directly onto a short pad of silica gel. Elution with 5% EtOAc-hexanes yielded the title compound as a brown oil (8.77 g, 95%).

$^1$H NMR (300 MHz, CDCl$_3$): δ 0.96 (t, J=7.5 Hz, 3H), 1.11 (t, J=7.3 Hz, 3H), 1.23 (2d, J=6.7 Hz, 12H), 1.68 (m, 2H), 2.65 (m, 2H), 2.86 (hept, J=6.9 Hz, 1H), 3.31 (hept, J=6.9 Hz, 1H), 3.59(t, J=6.5 Hz, 2H), 6.11 (dt, J=8.2, 1.5 Hz, 1H), 6.77 (d, J=2.3 Hz, 1H), 7.11 (d, J=2.1 Hz, 1H), 9.48 (d, J=8.2 Hz, 1H).

7-(3,5-Diisopropyl-2-propoxy-phenyl)-3-methyl-nona-2,4,6-trienoic acid ethyl ester (Compound 7)

To a solution of 4-(diethoxy-phosphoryl)-3-methyl-but-2-enoic acid ethyl ester (10.6 mL, 43.6 mmol) in 1,3-dimethyl-3,4,5,6-tetrahydro-2(1H)-pyrimidinone (DMPU, 20 mL) and THF (80 mL) at −78° C. was added n-BuLi dropwise (1.6 M in hexanes, 27.2 mL, 43.6 mmol). After 10 min, 3-(3,5-diisopropyl-2-propoxy-phenyl)-pent-2-enal (Intermediate 6, 8.77 g, 29.0 mmol) in THF (15 mL and 5 mL rinse) was added slowly to the reaction. The mixture was stirred at −78° C. for 2h, was quenched with saturated NH$_4$Cl and extracted with EtOAc. The organic layer was separated, washed successively with H$_2$O, brine, dried over Na$_2$SO$_4$, and concentrated in vacuo. The residue was purified by flash column chromatography on silica gel (2.5% EtOAc-hexanes) to yield the title compound as a yellow syrup (11.4 g, 95%).

$^1$H NMR (300 MHz, CDCl$_3$): δ 0.95 (t, J=7.5 Hz, 3H), 1.03 (t, J=7.5 Hz, 3H), 1.22 (2d, J=6.7 Hz, 12H), 1.27 (t, J=7.2 Hz, 3H), 1.66 (m, 21), 2.13 (d, J=1.2 Hz, 3H), 2.56 (br q, J=7.3 Hz, 2H), 2.85 (hept, J=6.9 Hz, 1H), 3.33 (hept, J=6.9 Hz, 1H), 3.68 (m, 2H), 4.15 (q, J=7.2 Hz, 2H), 5.73 (s, 1H), 6.22 (d, J=10.9 Hz, 1H), 6.24 (d, J=15.3 Hz, 1H), 6.59 (dd, J=15.1, 11.0 Hz, 1H), 6.71 (d, J=2.4 Hz, 1H), 7.03 (d, J=2.4 Hz, 1H).

7-(3,5-Diisopropyl-2-propoxy-phenyl)-3-methyl-nona-2,4,6-trienoic acid (Compound 8)

A solution of 7-(3,5-diisopropyl-2-propoxy-phenyl)-3-methyl-nona-2,4,6-trienoic acid ethyl ester (Compound 7, 11.4 g, 27.7 mmol) in EtOH (220 mL) was treated with 1M NaOH (111 mL, 111 mmol) and was heated to 80° C. for 3 h. The mixture was cooled to room temperature, acidified with 1M HCl (115 mL), and was extracted with EtOAc. The organic layer was separated, washed with brine, dried over Na$_2$SO$_4$, and concentrated in vacuo. The residue was purified by recrystallization from CH$_3$CN to yield the title compound as an off-white solid (7.56 g, 71%).

$^1$H NMR (300 MHz, CDCl$_3$): δ 0.95 (t, J=7.3 Hz, 3H), 1.03 (t, J=7.5 Hz, 3H), 1.23 (2d, J=7.0 Hz, 12H), 1.66 (m, 2H), 2.14 (d, J=0.9 Hz, 3H), 2.57 (br q, J=7.6 Hz, 2H), 2.85 (hept, J=6.7 Hz, 1H), 3.33 (hept, J=6.7 Hz, 1H), 3.58 (m, 2H), 5.76 (s, 1H), 6.23 (d, J=10.9 Hz, 1H), 6.27 (d, J=15.0 Hz, 1H), 6.63 (dd, J=15.1, 11.0 Hz, 1H), 6.71 (d, J=2.4 Hz, 1H), 7.04 (d, J=2.4 Hz, 1H).

2,4-Diisopropyl-phenol (Intermediate 1)

A mixture of 3,5-diisopropylsalicylic acid (Intermediate 9, 25 g, 0.11 mol, available from Aldrich) and quinoline (50 mL) was refluxed for 4 h. The mixture was cooled to room temperature, diluted with EtOAc (200 mL), washed with 1M HCl (2×200 mL) until acidic, then with brine, dried over Na$_2$SO$_4$, and concentrated in vacuo. The residue was purified by flash column chromatography on silica gel (5% then 10% EtOAc-hexanes) to yield the title compound as a yellow oil (20 g, ~100%).

$^1$H NMR (300 MHz, CDCl$_3$): □ 1.23 (d, J=6.7 Hz, 6H), 1.27 (d, J=6.7 Hz, 6H), 2.84 (m, 1H), 3.19 (m, 1H), 4.55 (br d, 1H), 6.68 (d, J=8.2 Hz, 1H), 6.83 (dd, J=8.2, 2.3 Hz, 1H), 7.05 (d, J=2.3 Hz, 1H).

6,8-Diisopropyl-4-methyl-chromen-2-one (Intermediate 11)

A mixture of 2,4-diisopropyl-phenol (Intermediate 1, 2.2 g, 12.4 mmol) and ethyl acetoacetate (4.0 mL, 30.9 mmol) was treated with 75% H$_2$SO$_4$ (12 mL, pre-mixed and cooled to 0° C.). The mixture was stirred at room temperature for 16 h, poured onto ice and extracted with EtOAc. The organic layer was separated, washed successively with saturated NaHCO$_3$, H$_2$O, and brine, dried over Na$_2$SO$_4$, and concentrated in vacuo. The residue was purified by flash column chromatography on silica gel (10% EtOAc-hexanes) to yield the tide compound as a light yellow syrup (2.6 g, 87%).

$^1$H NMR (300 MHz, CDCl$_3$): □ 1.29 (d, J=7.0 Hz, 6H), 1.30 (d, J=7.0 Hz, 6H), 2.45 (d, J=1.2 Hz, 3H), 2.98 (m, 1H), 3.63 (m, 1H), 6.28 (d, J=1.2 Hz, 1H), 7.34 (d,J=2.1 Hz, 1H).

2-(3-Hydroxy-1-methyl-propenyl)-4,6-diisopropyl-phenol (Intermediate 12)

To a solution of 6,8-diisopropyl-4-methylchromen-2-one Intermediate 11, 2.6 g, 10.7 mmol) in Et$_2$O (100 mL) at 0° C. was added LiAlH$_4$ portionwise (405 mg, 10.7 mmol). The reaction was stirred at 0° C. for 1 h, quenched by careful addition of ice, and acidified with 1M HCl. The mixture was then extracted with EtOAc. The organic layer was separated, washed successively with H$_2$O, brine, dried over Na$_2$SO$_4$, and concentrated in vacuo. The residue was purified by flash column chromatography on silica gel (20% EtOAc-hexanes) to yield the title compound as a nearly colorless syrup (1.82 g, 70%).

$^1$H NMR (300 MHz, CDCl$_3$): □ 1.22 (d, J=7.0 Hz, 6H), 1.25 (d, J=7.0 Hz, 6H), 2.06 (d, J=0.6 Hz, 3H), 2.83 (m, 1H), 3.28 (m, 1H), 3.94 (d, J=7.3 Hz, 2H), 5.96 (td, J=7.0, 1.5 Hz, 1H), 6.71 (d, J=2.3 Hz, 1H), 6.98 (d, J=2.1 Hz, 1H).

3-(3.5-Diisopropyl-2-propoxy-phenyl)-but-2-en-1-ol (Intermediate 13)

To a solution of 2-(3-hydroxy-1-methyl-propenyl)-4,6-diisopropyl-phenol (Intermediate 12, 1.82 g, 7.3 mmol) and 1-iodopropane (0.79 mL, 8.1 mmol) in DMF (20 mL) at room temperature was added CsF (3.9 g, 25.6 mmol). The reaction was stirred at room temperature for 1.5 h, diluted with EtOAc, washed successively with H$_2$O, brine, dried over Na$_2$SO$_4$, and concentrated in vacuo. The residue was purified by flash column chromatography on silica gel (10% EtOAc-hexanes) to yield the title compound as an off-white solid (2.06 g, 97%).

¹H NMR (300 MHz, CDCl₃): □ 1.01 (t, J=7.3 Hz, 3H), 1.23 (d, J=6.7 Hz, 12H), 1.74 (m, 2H), 2.11 (d, J=0.9 Hz, 3H), 2.85 (m, 1H), 3.31 (m, 1H), 3.64 (t, J=6.7 Hz, 2H), 3.81 (d, J=7.6 Hz, 2H), 5.84 (td, J=7.3, 1.5 Hz, 1H), 6.75 (d, J=2.1 Hz, 1H),7.01 (d,J=2.4 Hz, 1H).

3-(3,5-Diisopropyl-2-propoxy-phenyl-but-2-enal (Intermediate 14)

To a solution of 3-(3,5-diisopropyl-2-propoxy-phenyl)-but-2-en-1-ol (Intermediate 13, 2.06 g, 7.1 mmol) and NMO (2.5 g, 21.3 mmol) in CH₂Cl₂ (10 mL) at 0° C. was added catalytic amount of TPAP. The reaction was stirred at room temperature for 45 min and then loaded directly onto a short pad of silica gel. Elution with 10% EtOAc-hexanes yielded the title compound as a yellow syrup (2.1 g, 100%).

¹H NMR (300 MHz, CDCl₃): □ 0.96 (t, J=7.3 Hz, 3H), 1.22 (d, J=7.0 Hz, 12H), 1.69 (m, 2H), 2.33 (d, J=1.2 Hz, 3H), 2.85 (m, 1H), 3.31 (m, 1H), 3.60 (t, J=6.5 Hz, 2H), 6.10 (dq, J=8.2, 1.5 Hz, 1H), 6.80 (d, J=2.4 Hz, 1H), 7.10 (d, J=2.4 Hz, 1H), 9.43 (d, J=8.2 Hz, 1H).

7-3,5-Diisopropyl-2-propoxy-phenyl)-3-methyl-octa-2,4,6-trienoic acid ethyl ester (Compound 15)

To a solution of 4-(diethoxy-phosphoryl)-3-methyl-but-2-enoic acid ethyl ester (3.4 mL, 14.2 mmol, in DMPU (16 mL) and THF (32 mL) at −78° C. was added n-BuLi dropwise (1.6 M in hexanes, 8.9 mL, 14.2 mmol). After 10 min, 3-(3,5-diisopropyl-2-propoxy-phenyl)-but-2-enal (Intermediate 14, 2.1 g, 7.1 mmol) in THF (8 mL) was added slowly to the reaction. The mixture was stirred at −78° C. for 1 h, and was quenched with saturated NH₄Cl, extracted with EtOAc.

The organic layer was separated, washed successively with H₂O, brine, dried over Na₂SO₄, and concentrated in vacuo. The residue was purified by flash column chromatography on silica gel (4% EtOAc-hexanes) to yield the title compound as a yellow syrup (2.45 g, 87%).

¹H NMR (300 MHz, CDCl₃): □ 0.95 (t, J=7.3 Hz, 3H), 1.22 (d, J=6.7 Hz, 6H), 1.23 (d, J=7.0 Hz, 3H), 1.27 (d, J=7.0 Hz, 3H), 1.66 (m, 2H), 2.13 (d, J=1.2 Hz, 3H), 2.19 (br s, 3H), 2.84 (m, 1H), 3.32 (m, 1H), 3.58 (t, J=6.2 Hz, 2H), 4.14 (q, J=7.3 Hz, 2H), 5.72 (s, 1H), 6.20 (d, J=15.5 Hz, 1H), 6.21 (d, J=10.6 Hz, 1H), 6.56 (dd, J=15.8, 10.3 Hz, 1H), 6.74 (d, J=2.3 Hz, 1H), 7.02 (d, J=2.3 Hz, H1).

7-(3,5-Diisopropyl-2-propoxy-phenyl)-3-methyl-octa-2,4, 6-trienoic acid (Compound 16)

A solution of 7-(3,5-diisopropyl-2-propoxy-phenyl)-3-methyl-octa-2, 4,6-trienoic acid ethyl ester (Compound 15, 2.45 g, 6.16 mmol) in EtOH (50 mL) was treated with 1M NaOH (25 mL, 25 mmol) and was heated to 80° C. for 4 h. The mixture was cooled to room temperature, acidified with 1M HCl, and was extracted with EtOAc. The organic layer was separated, washed with brine, dried over Na₂SO₄, and concentrated in vacuo. The residue was purified by recrystallization from CH₃CN to yield the title compound as a white solid (1.87 g, 82%).

¹H NMR (300 MHz, CDCl₃): □ 0.95 (t, J=7.3 Hz, 3H), 1.22 (d, J=6.7 Hz, 6H), 1.23 (d, J=7.0 Hz, 6H), 1.66 (m, 2H), 2.13 (d, J=1.2 Hz, 3H),2.20 (br s, 3H), 2.85 (m, 1H), 3.32 (m, 1H), 3.58 (t, J=6.2 Hz, 2H), 5.75 (s, 1H), 6.22 (d, J=10.9 Hz, 1H), 6.23 (d, J=15.3 Hz, 1H), 6.61 (dd, J=15.3, 10.8 Hz, 1H), 6.74 (d, J=2.4 Hz, 1H), 7.03 (d, J=2.4 Hz, 1H).

BIOLOGICAL ACTIVITY, MODES OF ADMINISTRATION

It has been discovered in accordance with the present invention that compounds of this invention are capable of significantly reducing serum glucose levels and reducing or maintaining serum triglyceride levels in diabetic mammals, without the undesirable side effects of reducing serum thyroxine levels (hypothyroidism) and transiently raising triglyceride levels (hypertriglyceridemia). The compounds of the invention are partial agonists of the RXRs.

Table 1 below discloses the results of certain assays where the compounds of the invention were tested as agonists of RAR and RXR retinoid receptors.

One such assay is a chimeric receptor transactivation assay which tests for agonist-like activity in the $RAR_\alpha$, $RAP_\beta$ and $RAR_\gamma$ receptor subtypes, and which is based on work published by Feigner P. L. and Holm M. (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO W093/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay. The results of the ligand binding assay are expressed in $K_i$ numbers. (See Cheng et al. Biochemical Pharmacology Vol. 22 pp 3099–3108, expressly incorporated herein by reference.)

Efficacy in a transactivation assay is expressed as a percentage of the maximum potency attained by the compound compared to a standard which, in this case, is the compound named (2E, 4E, 1'S, 2'S)-3-methyl-5-[2'-methyl-2'-(5,5,8,8-tetramethyl-5,6,7,8-tetrahydro-naphthalen-2-yl)-cyclopropyl]-penta-2, 4-dienoic acid . This standard compound is described in U.S. Pat. No. 6,114,533.

Table 1 discloses the activity of certain exemplary compounds of the invention in the above-described receptor transactivation and binding assays. Particularly, the transactivation data pertaining to activation of the RAR receptors were obtained in the chimeric assay, and the transactivation data pertaining to the activation of RXR receptors were obtained in the holoreceptor assay. In the chimeric receptor transactivation assay the compounds were essentially inactive in activating $RAR_\alpha$, $RAR_\beta$ and $RAR_\gamma$ receptors.

TABLE 1

| Compound Number | Structure | RAR Trans. EC$_{50}$ nM RAR Bind. K$_i$ nM | | | RXR Trans. EC$_{50}$ nM RXR Bind. K$_i$ nM | | |
|---|---|---|---|---|---|---|---|
| | | α | β | γ | α | β | γ |
| Standard compound | [structure] | NA >10 k | NA >10 k | NA >10 k | 0.08 (100) 1 | 0.4 (100) 1 | 0.09 (100) 1 |
| 16 | [structure] | NA 310 | NA 200 | NA 550 | 0.4 (34) 1 | 4 (33) 12 | 1 (25) 21 |
| 8 | [structure] | NA 170 | NA 80 | NA 310 | 1 (33) 1 | 8 (29) 12 | 6 (21) ND |

In Table 1, NA stands for not active at all as an agonist and ND stands for not determined. The first row of numbers pertaining to each compound is the measured EC$_{50}$ number. The second row of numbers indicates efficacy as a percentage compared to the standard compound, (2E, 4E, 1'S, 2'S)-3-methyl-5-[2'-methyl-2'-(5,5,8,8-tetramethyl-5,6,7,8-tetrahydro-naphthalen-2-yl)-cyclopropyl]-penta-2,4-dienoic acid. The third row of numbers pertaining to each compound is the binding K$_i$ number.

An assay described below tests the effect of compounds of the invention on serum glucose, tryglyceride and thyroxine levels in female 9–10 weeks old db/db mice.

Description of Assay

Female diabetic db/db (9–10 weeks old) mice were maintained on standard laboratory food and treated by oral gavage with vehicle (corn oil), standard compound (2E, 4E, 1'S, 2'S)-3-methyl-5-[2'-methyl-2'5,5,8,8-tetramethyl-5,6,7,8-tetrahydro-naphthalen-2-yl)-cyclopropyl]-penta-2,4-dienoic acid (5 mg/kg) or the test compound (5–100 mg/kg, as described in Table 2) daily for seven days at 8:00 AM. Blood samples (70 μl) were taken by orbital bleeding at 11:00 AM on day 0 (pre-treatment), day 3, and day 6. On day 7, a blood sample (700 μl) was taken at 11:00 AM and the animals were sacrificed. Glucose, triglyceride and thyroxine (T4) levels were determined on a Boehringer Manheim Hatachi Clinical Chemistry Analyzer using standard protocols provided by the manufacturer and reagents that were supplied in commercially available kits (glucose and T4: Boehringer Manheim; triglycerides: Roche Diagnostics). Seven animals were treated in each group. The results of the assays are summarized in Tables 2 and 3.

TABLE 2

Glucose, Triglycerides, and Thyroxine (T4) in Female db/db mice (9–10 weeks old) treated with Vehicle, Standard Compound and Compound 16.

| | Glucose (mg/dl) | | | Triglycerides (mg/dl) | | T4 (μg/dL) |
|---|---|---|---|---|---|---|
| Treatment (dose) | Day 0 | Day 3, 3 h | Day 6, 3 h | Day 0 | Day 3, 3 h | Day 7 |
| Vehicle (Corn oil) | 380 ± 104 | 441 ± 109 | 493 ± 123 | 207 ± 89 | 246 ± 55 | 2.2 ± 0.5 |
| Standard compound (5 mg/kg) | 378 ± 64 | 308 ± 84 | 333 ± 79 | 171 ± 84 | 472 ± 312 | 1.2 ± 0.2 |
| Compound 16 (50 mg/kg) | 365 ± 81 | 283 ± 80 | 309 ± 109 | 199 ± 139 | 189 ± 90 | 2.2 ± 0.4 |

TABLE 3

Glucose, Triglycerides, and Thyroxine (T4) in Female db/db mice (9–10 weeks old) treated with Vehicle, Standard Compound and Compound 8.

| | Glucose (mg/dl) | | | Triglycerides (mg/dl) | | T4 (μg/dL) |
|---|---|---|---|---|---|---|
| Treatment (dose) | Day 0 | Day 3, 3 h | Day 6, 3 h | Day 0 | Day 3, 3 h | Day 7 |
| Vehicle (Corn oil) | 396 ± 75 | 487 ± 129 | 537 ± 251 | 259 ± 68 | 303 ± 145 | 2.1 ± 0.8 |

TABLE 3-continued

Glucose, Triglycerides, and Thyroxine (T4) in Female db/db mice (9–10 weeks old) treated with Vehicle, Standard Compound and Compound 8.

| Treatment (dose) | Glucose (mg/dl) | | | Triglycerides (mg/dl) | | T4 |
| --- | --- | --- | --- | --- | --- | --- |
| | Day 0 | Day 3, 3 h | Day 6, 3 h | Day 0 | Day 3, 3 h | (µg/dL) Day 7 |
| Standard compound (5 mg/kg) | 409 ± 122 | 369 ± 121 | 378 ± 125 | 193 ± 82 | 50 ± 121 | 1.4 ± 0.6 |
| Compound 8 (50 mg/kg) | 468 ± 149 | 443 ± 104 | 384 ± 114 | 173 ± 30 | 278 ± 48 | 3.0 ± 0.7 |

As the data indicate, the compounds of the invention not only cause significant decrease in serum glucose levels and maintain or reduce triglyceride levels in diabetic mammals, but in contrast with the prior art standard compound (2E, 4E, 1'S, 2'S)-3-methyl-5-[2'-methyl-2'-(5,5,8,8-tetramethyl-5,6,7,8-tetrahydro-naphthalen-2-yl)-cyclopropyl]-penta-2,4-dienoic acid do not have the undesirable side effect of reducing serum thyroxine levels.

MODES OF ADMINISTRATION, DOSING

To treat diabetic mammals, including humans for the purpose of reducing serum glucose levels in said mammals a pharmaceutical composition containing one or more compound of the invention is administered to the mammal in daily doses in the range of 1 to 100 mg per kg body weight of the mammal. Preferably the daily dose is between 10 to 50 mg per kg body weight of the mammal.

Generally speaking the compounds of the invention are also useful for preventing or treating diseases and conditions that are responsive to compounds that promote the expression of or bind to receptors belonging to the steroid or thyroid receptor superfamily. More specifically the compounds of the invention can be used for preventing or treating skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. The compounds are also useful for the prevention and treatment of metabolic diseases and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without 'imitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

To treat diabetes the compounds of this invention are preferably administered, orally.

For the prevention or treatment of other diseases or conditions the compounds of the invention may be administered systemically or topically, depending on such considerations as the condition to be treated, need for site-specific treatment, quantity of drug to be administered, and numerous other considerations. Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pennsylvania. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition. A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 1 and 50 mg per kg of body weight per day would be expected to effect a therapeutic result in the treatment of many diseases for which these compounds are useful.

What is claimed is:

1. A compound of the formula

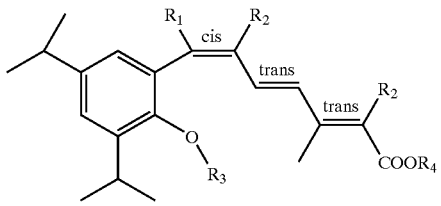

where $R_1$ is alkyl of 1 to 3 carbons;

R2 is independently H or F;

R3 is propyl or iso-propyl, and

R4 is H, alkyl of 1 to 6 carbons, $CH_2OR_5$ or $CH_2OCOR_5$ where $R_5$ is alkyl of 1 to 3 carbons, or a pharmaceutically acceptable salt of said compound.

2. A compound in accordance with claim 1 where $R_1$ is methyl or ethyl.

3. A compound in accordance with claim 1 where $R_2$ is H.

4. A compound in accordance with claim 1 where $R_3$ is propyl.

5. A compound in accordance with claim 1 where $R_4$ is H, alkyl of 1 to 3 carbons, or a pharmaceutically acceptable salt of said compound.

6. A compound of the formula

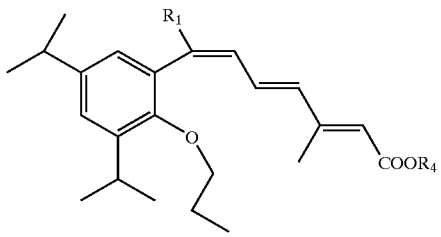

where $R_1$ is methyl or ethyl, and $R_4$ is H, alkyl of 1 to 6 carbons, $CH_2OR_5$ or $CH_2OCOR_5$ where $R_5$ is alkyl of 1 to 3 carbons, or a pharmaceutically acceptable salt of said compound.

7. A compound in accordance with claim 6 where $R_4$ is H, alkyl of 1 to 3 carbons, or a pharmaceutically acceptable salt of said compound.

8. A compound in accordance with claim 6 where $R_1$ is methyl.

9. A compound in accordance with claim 8 where $R_4$ is H. or ethyl, or a pharmaceutically acceptable salt of said compound.

10. A compound in accordance with claim 6 where $R_1$ is ethyl.

11. A compound in accordance with claim 10 where $R_4$ is H, or ethyl, or a pharmaceutically acceptable salt of said compound.

12. A process for administering to a diabetic mammal to reduce the serum glucose level of said mammal a compound of the formula

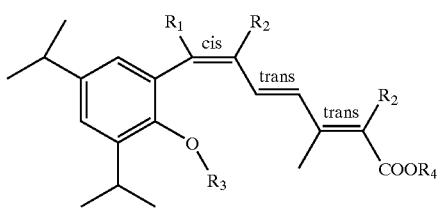

where $R_1$ is alkyl of 1 to 3 carbons;

$R_2$ is independently H or F;

$R_3$ is propyl or iso-propyl, and $R_4$ is H, alkyl of 1 to 6 carbons, $CH_2OR_5$ or $CH_2OCOR_5$ where $R_5$ is alkyl of 1 to 3 carbons, or a pharmaceutically acceptable salt of said compound.

13. A process in accordance with claim 12 where the compound used in the process is in accordance with the formula

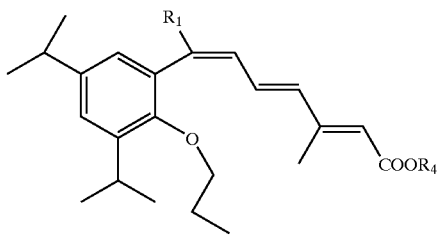

where $R_1$ is methyl or ethyl, and $R_4$ is H, alkyl of 1 to 6 carbons, $CH_2OR_5$ or $CH_2OCOR_5$ where $R_5$ is alkyl of 1 to 3 carbons, or a pharmaceutically acceptable salt of said compound.

14. A process in accordance with claim 13 where in the compound of the formula $R_1$ is methyl.

15. A process in accordance with claim 14 where in the compound of the formula $R_4$ is H, or ethyl, or a pharmaceutically acceptable salt of said compound.

16. A process in accordance with claim 13 where in the compound of the formula $R_1$ is ethyl.

17. A process in accordance with claim 16 where in the compound of the formula $R_4$ is H, or ethyl, or a pharmaceutically acceptable salt of said compound.

* * * * *

UNITED STATES PATENT AND TRADEMARK OFFICE
CERTIFICATE OF CORRECTION

PATENT NO. : 6,759,546 B1
DATED : July 6, 2004
INVENTOR(S) : Vasudevan et al.

It is certified that error appears in the above-identified patent and that said Letters Patent is hereby corrected as shown below:

Column 8,
Line 26, "3.29 (hept, J=7.0Hz, M1)" should be -- 3.29 (hept, J=7.0Hz, 1H) --
Line 62, "1.86 (m,2)" should be -- 1.86 (m, 2H) --

Column 9,
Line 54, "1.66 (m, 21)" should be -- 1.66 (m, 2H) --

Column 10,
Line 35, "the tide" should be -- the title --

Column 11,
Line 14, "(2.1 g, 100%)" should be (2.1 g, ~100%) --
Line 42, "7.02 (d, J=2.3Hz, H1)" should be -- 7.02 (d, J=2.3Hz, 1H) --

Column 14,
Table 1,

"

| Compound Number | Structure | RAR Trans. EC$_{50}$ nM / RAR Bind. K$_i$ nM | | | RXR Trans. EC$_{50}$ nM / RXR Bind K$_i$ nM | | |
|---|---|---|---|---|---|---|---|
| | | α | β | γ | α | β | γ |
| Standard compound | 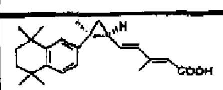 | NA >10k | NA >10k | NA >10k | 0.08(10) 1 | 0.4(100) 1 | 0.09(100) 1 |
| 16 | 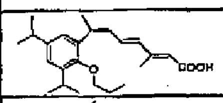 | NA 310 | NA 200 | NA 550 | 0.4(34) 1 | 4(33) 12 | 1(25) 21 |
| 8 | 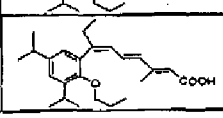 | NA 170 | NA 80 | NA 310 | 1(33) 1 | 6(29) 12 | 6(21) ND |

"

should be
--

| Compound Number | Structure | RAR Trans. EC$_{50}$ nM / RAR Bind. K$_i$ nM | | | RXR Trans. EC$_{50}$ nM / RXR Bind K$_i$ nM | | |
|---|---|---|---|---|---|---|---|
| | | α | β | γ | α | β | γ |
| Standard compound | 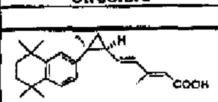 | NA >10k | NA >10k | NA >10k | 0.08 (100) 1 | 0.4 (100) 1 | 0.09 (100) 1 |
| 16 | 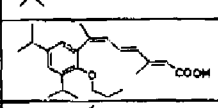 | NA 310 | NA 200 | NA 550 | 0.4 (34) 1 | 4 (33) 12 | 1 (25) 21 |
| 8 | 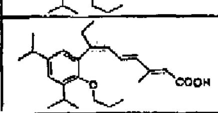 | NA 170 | NA 80 | NA 310 | 1 (33) 1 | 6 (29) 12 | 6 (21) ND |

--

UNITED STATES PATENT AND TRADEMARK OFFICE
CERTIFICATE OF CORRECTION

PATENT NO. : 6,759,546 B1
DATED : July 6, 2004
INVENTOR(S) : Vasudevan et al.

It is certified that error appears in the above-identified patent and that said Letters Patent is hereby corrected as shown below:

Column 14 (cont'd),
Table 2,
"

| Treatment (dose) | Glucose (mg/dl) | | | Triglycerides (mg /dl) | | T4 |
|---|---|---|---|---|---|---|
| | Day 0 | Day 3, 3h | Day 6, 3h | Day 0 | Day 3, 3h | (µg/dL) Day 7 |
| Vehicle (Corn oil) | 380 ± 104 | 441 ± 109 | 493 ± 123 | 207 ± 89 | 246 ± 55 | 2.2 ± 0.5 |
| Standard compound (5 mg/kg) | 378 ± 64 | 308 ± 84 | 333 ± 79 | 171 ± 84 | 472 ± 312 | 1.2 ± 0.2 |
| Compound 16 (50 mg/kg) | 365 ± 81 | 283 ± 80 | 309 ± 109 | 199 ± 139 | 189 ± 90 | 2.2 ± 0.4 |

"

should be

--

| Treatment (dose) | Glucose (mg/dl) | | | Triglycerides (mg /dl) | | T4 (µg/dL) |
|---|---|---|---|---|---|---|
| | Day 0 | Day 3, 3h | Day 6, 3h | Day 0 | Day 3, 3h | Day 7 |
| Vehicle (Corn oil) | 380 ± 104 | 441 ± 109 | 493 ± 123 | 207 ± 89 | 246 ± 55 | 2.2 ± 0.5 |
| Standard compound (5 mg/kg) | 378 ± 64 | 308 ± 84 | 333 ± 79 | 171 ± 84 | 472 ± 312 | 1.2 ± 0.2 |
| Compound 16 (50 mg/kg) | 365 ± 81 | 283 ± 80 | 309 ± 109 | 199 ± 139 | 189 ± 90 | 2.2 ± 0.4 |

--

Table 3,
"

| Treatment (dose) | Glucose (mg/dl) | | | Triglycerides (mg /dl) | | T4 |
|---|---|---|---|---|---|---|
| | Day 0 | Day 3, 3h | Day 6, 3h | Day 0 | Day 3, 3h | (µg/dL) Day 7 |
| Vehicle (Corn oil) | 396 ± 75 | 487 ± 129 | 537 ± 251 | 259 ± 68 | 303 ± 145 | 2.1 ± 0.8 |
| Standard compound (5 mg/kg) | 409 ± 122 | 369 ± 121 | 378 ± 125 | 193 ± 82 | 503 ± 121 | 1.4 ± 0.6 |
| Compound 8 (50 mg/kg) | 468 ± 149 | 443 ± 104 | 384 ± 114 | 173 ± 30 | 278 ± 48 | 3.0 ± 0.7 |

"

UNITED STATES PATENT AND TRADEMARK OFFICE
CERTIFICATE OF CORRECTION

PATENT NO. : 6,759,546 B1
DATED : July 6, 2004
INVENTOR(S) : Vasudevan et al.

It is certified that error appears in the above-identified patent and that said Letters Patent is hereby corrected as shown below:

Column 14 (cont'd),
should read

| Treatment (dose) | Glucose (mg/dl) | | | Triglycerides (mg/dl) | | T4 (µg/dL) |
|---|---|---|---|---|---|---|
| | Day 0 | Day 3, 3h | Day 6, 3h | Day 0 | Day 3, 3h | Day 7 |
| Vehicle (Corn oil) | 396 ± 75 | 487 ± 129 | 537 ± 251 | 259 ± 68 | 303 ± 145 | 2.1 ± 0.8 |
| Standard compound (5 mg/kg) | 409 ± 122 | 369 ± 121 | 378 ± 125 | 193 ± 82 | 503 ± 127 | 1.4 ± 0.6 |
| Compound 8 (50 mg/kg) | 468 ± 149 | 443 ± 104 | 384 ± 114 | 173 ± 30 | 278 ± 48 | 3.0 ± 0.7 |

Column 17,
Line 54, "$R_4$ is H." should be -- $R_4$ is H, --

Signed and Sealed this

Twelfth Day of July, 2005

JON W. DUDAS
*Director of the United States Patent and Trademark Office*

Disclaimer

6,759,546—Jayasree Vasudevan, Anaheim, CA (US); Richard L. Beard, Newport Beach, CA (US); Haiqing Yuan, Irvine, CA (US); Roshantha A. Chandratratna, Laguna Hills, CA (US). 3,5-DI-ISO-PROPYL-HEPTATRIENOIC ACID DERIVATIVES HAVING SERUM GLUCOSE REDUCING ACTIVITY. Patent dated July 6, 2004. Disclaimer filed August 8, 2011, by the assignee, Allergan, Inc., Irvine, CA (US).

Hereby disclaims all of the claims 1-17 of said patent.

*(Official Gazette November 22, 2011)*